United States Patent [19]
Imamura et al.

[11] Patent Number: 5,874,254
[45] Date of Patent: Feb. 23, 1999

[54] FGF-5 ANALOGOUS PROTEIN, AND PHARMACEUTICAL COMPOSITION CONTAINING THE SAME

[75] Inventors: Toru Imamura, Tokyo; Syuichi Oka, Ibaraki; Kazuo Ozawa, Chiba; Chieri Sato; Seigo Suzuki, both of Ibaraki, all of Japan

[73] Assignee: Director-General of Agency of Industrial Science and Technology, Tokyo, Japan

[21] Appl. No.: 822,573

[22] Filed: Mar. 19, 1997

[30] Foreign Application Priority Data

Mar. 29, 1996 [JP] Japan .................................. 8-075994

[51] Int. Cl.⁶ .......................... A61K 38/18; C07K 14/50; C12N 15/16
[52] U.S. Cl. ............................ 435/69.4; 514/12; 530/399
[58] Field of Search ........................... 530/399; 435/69.4; 514/12

[56] References Cited

PUBLICATIONS

"The rate FGF–5 mRNA variant generated by alternative splicing encodes a novel truncated from of FGF–5" by Hattori et al.; Biochimica et Biophysica Acta 1306 (1996) pp. 31–33.

"The Human FGF–5 Oncogene Encodes a Novel Protein Related to Fibroblast Growth Factors" by Zhan et al.; Molecular and Cellular Biology, Aug. 1988, pp. 3487–3495.

"Expression of the murine fibroblast growth factor 5 gene in the adult central nervous system" by Haub et al.; Proc. Natl. Acad. Sci. USA, vol. 87, pp. 8022–8026, Oct. 1990, Neurobiology.

*Primary Examiner*—Elizabeth Kemmerer
*Assistant Examiner*—Christine Saoud
*Attorney, Agent, or Firm*—Baker & Botts, L.L.P.

[57] ABSTRACT

The present invention relates to a novel FGF-5 analogous protein derived from mature mRNA formed by directly binding exon 1 to exon 3 in the splicing of a gene coding for FGF-5 protein as well as to a pharmaceutical composition containing the same as an active ingredient. The pharmaceutical composition containing the novel FGF-5 analogous protein of the present invention as an active ingredient can regulate physiological functions of FGF-5, such as regulation of restoration or development of hairs on the head and body, regulation of trophic and functional regulation in the brain and nervous system, proliferation of fibroblasts, etc.

8 Claims, 3 Drawing Sheets

FIG.1

Human FGF-5 Analog

```
         10        20        30        40        50        60
atgagcttgtccttcctcctcctcctcttcttcagccacctgatcctcagcgcctgggct
 M  S  L  S  F  L  L  L  F  F  S  H  L  I  L  S  A  W  A 70        80        90       100       110       120
cacggggagaagcgtctcgcccccaaagggcaacccggacccgctgccactgataggaac
 H  G  E  K  R  L  A  P  K  G  Q  P  G  P  A  A  T  D  R  N 130       140       150       160       170       180
cctataggctccagcagcagacagagcagcagtagcgctatgtcttcctcttctgcctcc
 P  I  G  S  S  S  R  Q  S  S  S  S  A  M  S  S  S  S  A  S 190       200       210       220       230       240
tcctcccccgcagcttctctgggcagccaaggaagtggcttggagcagagcagtttccag
 S  S  P  A  A  S  L  G  S  Q  G  S  G  L  E  Q  S  S  F  Q 250       260       270       280       290       300
tggagcccctcggggcgccggaccggcagcctctactgcagagtgggcatcggtttccat
 W  S  P  S  G  R  R  T  G  S  L  Y  C  R  V  G  I  G  F  H 310       320       330       340       350       360
ctgcagatctacccggatggcaaagtcaatggatcccacgaagccaatatgttaagccaa
 L  Q  I  Y  P  D  G  K  V  N  G  S  H  E  A  N  M  L  S  Q 370
gttcacagatga
 V  H  R  *
```

FIG.2

Mouse FGF-5 Analog

```
         10        20        30        40        50        60
atgagcctgtccttgctcttcctcatcttctgcagccacctgatccacagcgcttgggct
 M  S  L  S  L  L  F  L  I  F  C  S  H  L  I  H  S  A  W  A 70        80        90       100       110       120
cacggggagaagcgtctcactcccgaagggcaacccgcgcctcctaggaacccgggagac
 H  G  E  K  R  L  T  P  E  G  Q  P  A  P  P  R  N  P  G  D 130       140       150       160       170       180
tccagcggcagccggggcagaagtagcgcgacgttttcttcgtcttctgcctcctcacca
 S  S  G  S  R  G  R  S  S  A  T  F  S  S  S  S  A  S  S  P 190       200       210       220       230       240
gtcgcagcttctccgggcagccaaggaagcggctcggaacatagcagtttccagtggagc
 V  A  A  S  P  G  S  Q  G  S  G  S  E  H  S  S  F  Q  W  S 250       260       270       280       290       300
ccttcggggcgccggaccggcagcctgtactgcagagtgggcatcggtttccatctgcag
 P  S  G  R  R  T  G  S  L  Y  C  R  V  G  I  G  F  H  L  Q 310       320       330       340       350       360
atctacccggatggcaaagtcaatggctcccacgaagccagtgtgttaagccaaatttac
 I  Y  P  D  G  K  V  N  G  S  H  E  A  S  V  L  S  Q  I  Y 366
ggatga
 G  *
```

FIG.3

FGF-5 ANALOGOUS PROTEIN, AND PHARMACEUTICAL COMPOSITION CONTAINING THE SAME

FIELD OF THE INVENTION

The present invention relates to fibroblast growth factor-5 (FGF-5) analogous protein encoded by mRNA occurring by the alternative splicing of a gene encoding FGF-5 protein, as well as a pharmaceutical composition containing the same as an active ingredient, particularly a pharmaceutical composition useful for regulation of restoration or development of hairs on the head or body, trophic or functional regulation in the brain and nervous system and regulation of proliferation of fibroblasts etc.

BACKGROUND OF THE INVENTION

Conventionally, almost all components effective for promotion or suppression of restoration or development of hairs on the head or body have been obtained by screening synthetic compounds or natural substances in plants or microorganisms for those having such activity in e.g. experimental animals. However, because the trophic environments of hair roots were believed to be essential, conventional developments in hair restoration promoting agents, hair restoration suppressing agents and hair developing agents were based on improvement or suppression of topical blood circulation or environmental conditions for hair roots, but not on the mechanism of production of animal hairs.

Fibroblast growth factor-5 (FGF-5) is known to have growth promoting activity and transforming activity on fibroblasts as its physiological functions. If NIH3T3 fibroblasts are transformed with an FGF-5 gene under the control of a constant-expression vector, their growth ability is known to be altered by FGF-5. Also, FGF-5 secreted from these transformed cells into the culture significantly promotes the proliferation ability of other fibroblast BALB/c3T 3 cells. Further, an FGF-5 polypeptide expressed by *E. coli* transformed with an FGF-5 gene expression plasmid significantly promotes the proliferation ability of BALB/c3T3 as well.

The activity of FGF-5 as a neurotrophic factor is also known and expressed in skeletal muscle cells. Both FGF-5 contained in an extract of these skeletal muscle cells and FGF-5 expressed in the *E. coli* transformed with the FGF-5 gene expression plasmid are known to significantly promote the survival of cultured motor neurons. This fact strongly suggests that FGF-5 is a trophic factor of motor neurons. The expression of FGF-5 in mouse and rat brains was further found and it is believed from an experiment with brain nerve primary culture cells that FGF-5 acts as a trophic factor of cholinergic and serotonergic neurons in the brain.

The activity of FGF-5 as a neurotrophic factor came to be known as described above, and much attention is paid to a regulatory factor for the activity, but none of such regulatory factor has been found.

In the generation of the FGF-5 protein, it is known that a gene coding for the FGF-5 protein is transcribed into mRNA which in turn undergoes splicing such that exon 1, exon 2 and exon 3 are linked in this order to form a continuous chain in mature RNA. That is, its translational frame begins at the translational initiation codon ATG (coding for methionine) in exon 1, proceeds through exon 2 and ends at a termination codon in exon 3 to result in a protein composed of 268 amino acids in human or a protein of 264 amino acids in mouse (Zhan, X. et al., Mol. Cell. Biol., Vol. 8, pp. 3487–3495 (1988); Haub. O. et al., Proc. Natl. Acad. Sci., USA, Vol. 87, pp. 8022–8026 (1990)).

SUMMARY OF THE INVENTION

The object of the present invention is to provide a pharmaceutical composition useful for regulation of the physiological functions of FGF-5 e.g. regulation of hair restoration or development by direct action on the mechanism of hair production, trophic or functional regulation in the brain and nervous system, regulation of proliferation of fibroblasts, etc. as well as regulation of various physiological functions of FGF family proteins other than FGF-5 and of their gene products.

The present inventors paid attention to the presence of another FGF-5 mRNA besides the known one, and as a result of their eager research, they found that its coding protein regulates the physiological functions of FGF-5 and further that this protein acts on the fundamental mechanism of hair production to bring about regulation of hair restoration or development and trophic or functional regulation in the brain nerve system, and the present inventors arrived at completion of the present invention as a pharmaceutical composition containing the same.

That is, the present invention relates to a protein defined by splicing not known in the splicing step of generating mature mRNA (referred to as "post-translational alternative splicing of FGF-5 gene") as well as to a pharmaceutical composition containing the same.

DETAILED DESCRIPTION OF THE INVENTION

Hereinafter, the present invention is described in detail.

The novel FGF-5 protein of the present invention (referred to hereinafter as FGF-5 analogous protein) is derived from mature mRNA formed by directly binding exon 1 to exon 3 in the splicing of a gene coding for FGF-5 protein.

The FGF-5 analogous protein is identical with the known FGF-5 protein in the amino acid sequence (to the 118-position in human or to the 116-position in mouse) encoded by exon 1, but is different in the amino acid sequence beginning at the 119-position in human or the 117-position in mouse because exon 1 is linked directly to exon 3, and there appears a termination codon just after coding for amino acid 123 in human or amino acid 121 in mouse. Therefore, the FGF-5 analogous protein has a novel peptide-linked structure while having a partial structure of the FGF-5 protein.

Figure 1:
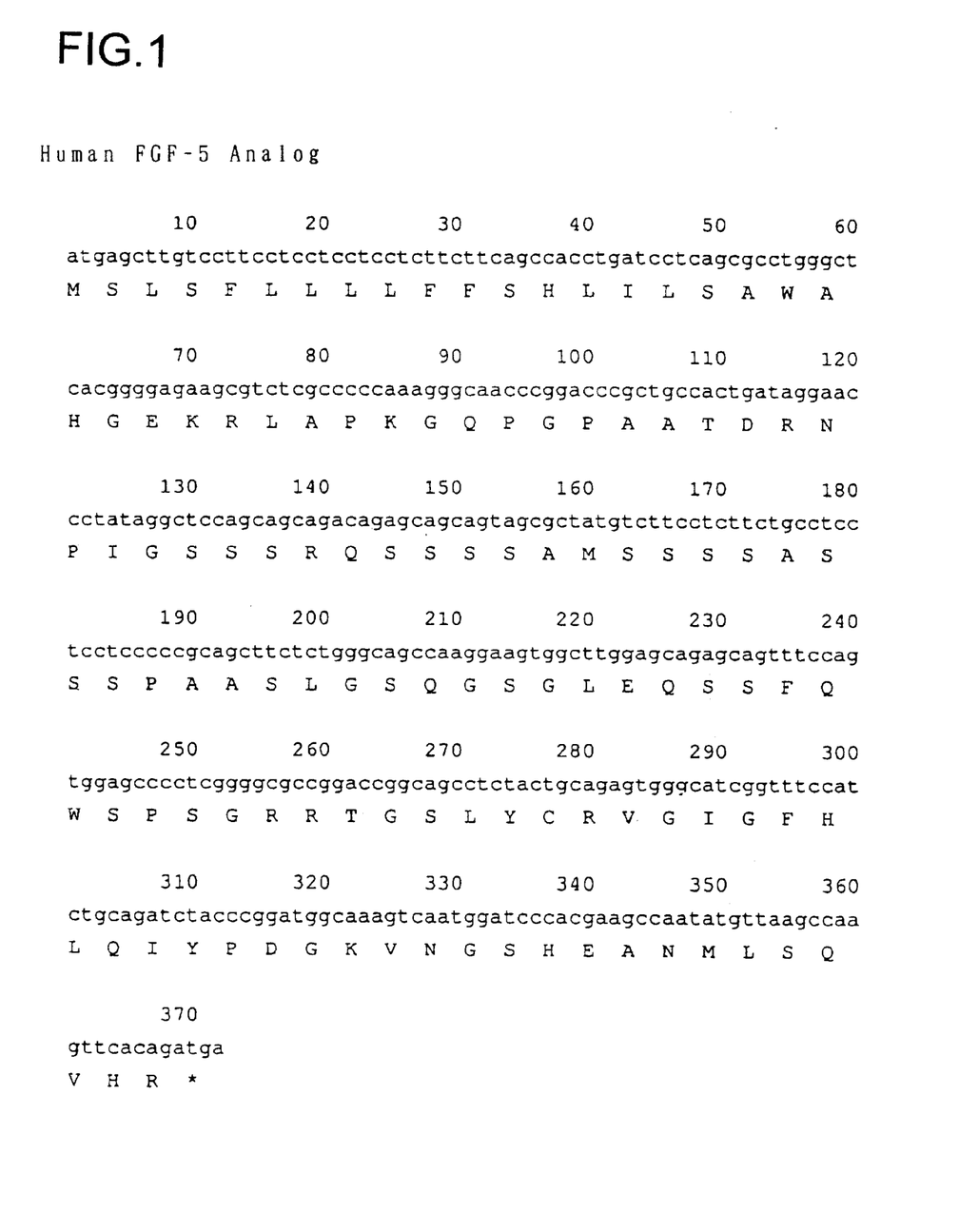
FIG. 1 shows the amino acid sequence (SEQ ID No:2) of human FGF-5 analogue (human FGF-5S) protein and a DNA sequence (SEQ ID No:1) coding for said protein.

The FGF-5 analogous protein of the present invention is specifically a protein having an amino acid sequence substantially shown in FIG. 1 (SEQ. ID No:2) for human and in FIG. 2 (SEQ. ID No:4) for mouse, and the former is encoded by the DNA sequence as shown in FIG. 1 (SEQ. ID No:1) and the latter by that in FIG. 2 (SEQ. ID No:3). The term "substantially" means that a part of said amino acid sequence may have undergone addition, deletion, replacement and modification unless its functions are lost.

The FGF-5 analogous protein referred to in the present invention includes not only a protein primarily defined by the cDNA shown in the Sequence Listing, but also a protein from which a peptide sequence called signal peptide present at the N-terminal when secreted from cells has been cleaved off. That is, the FGF-5 analogous protein contained as the active ingredient in the form of a recombinant etc. in the pharmaceutical composition of the present invention will not change its usefulness even if produced in the form of a signal peptide-free protein from the start.

Hereinafter, the method of preparing the FGF-5 analogous protein is specifically described.

RNA is extracted from animal brain tissues, and its reverse transcription is carried out using a random hexaoligonucleotide as a primer, followed by amplification by PCR techniques. If an oligonucleotide capable of amplifying the open reading frame in FGF-5 is used as the primer in reverse transcription, a DNA fragment corresponding in size to the FGF-5 protein analog of the present invention will be formed together with a DNA fragment corresponding in size to the known FGF-5 protein. The former is separated from the latter in gel electrophoresis, then cut off from the gel and inserted into a multicloning site in a cloning vector to give a plasmid.

The DNA may be integrated into any plasmid if it can be replicated and retained in a host. Examples are *E. coli*-derived pBR322, pUC18, and their derivatives such as pET-3c etc.

The DNA can be integrated into the plasmid as described e.g. by T. Maniatis et al. in Molecular Cloning, Cold Spring Harbor Laboratory, p. 239 (1982).

An expression vector can be obtained by linking the cloned gene to a region downstream of a promoter in a vector suitable for expression. Examples of such vectors are the above-described *E. coli*-derived plasmids (pBR322, pBR325, pUC12, pUC13, pET-3), *Bacillus subtilis*-derived plasmids (pUB110, pTP5, pC194), yeast-derived plasmids (pSH19, pSH15), bacteriophages such as λ -phage or their derivatives, animal viruses such as retrovirus, vaccinia virus etc., and insect viruses.

The 5'-terminal of said gene may possess ATG as the initiation codon, and the 3'-terminal may possess TAA, TGA or TAG as the termination codon. To express said gene, a promoter is linked to an upstream region. The promoter used in the present invention may be any promoter if it is suitable for a host used in gene expression. Examples of promoters are follows: a trp promoter, lac promoter, rec A promoter, λ PL promoter, lpp promoter, T7 promoter etc. for *E. coli* as the host transformed; SP01 promoter, SP02 promoter, penP promoter, etc. for *Bacillus subtilis* as the host; and PH05 promoter, PGK promoter, GAP promoter, ADH promoter etc. for yeast as the host. If the host is animal cells, SV40-derived promoter, retrovirus promoter etc. are used.

The thus constructed vector containing the nucleotide sequence coding for the FGF-5 analogous protein is used to produce a transformant carrying said vector.

The host includes *E. coli* (e.g. BL21, BL21 (DE3), BL21 (DE3) pLsS, BL21(DE3) pLysE), *Bacillus subtilis* (e.g.*Bacillus subtilis* DB105), yeast (e.g.*Pichia pastoris, Saccharomyces cerevisiae*), animal cells (e.g. COS cell, CHO cell, BHK cell, NIH3T3 cell, BALB/c3T3 cell, HUVE cell, LEII cell), and insect cells.

The transformation may be carried out in a usual manner. A peculiar method can also be used if it is applicable. If the host is *E. coli*, heat shock or electroporation is used to introduce the vector containing the recombinant DNA into competent cells prepared in the calcium method or any other method. If the host is yeast, heat shock or electroporation is used to introduce the vector containing the recombinant DNA into competent cells prepared in the lithium method or any other method. If the host is animal cells, the calcium phosphate method, lipofection method or electroporation is used to introduce the vector containing the recombinant DNA into cells at the proliferation phase etc.

The FGF-5 analogous protein is produced by culturing the resulting transformant in a medium.

To culture the transformant, the medium is that generally used for a desired host. A peculiar method can also be used if it is applicable. If the host is *E. coli*, LB medium etc. may be used. If the host is yeast, YPD medium etc. may be used. If the host is animal cells, Dulbecco's MEM supplemented with animal serum etc. may be used. The culture is carried under conventional conditions for a desired host. Peculiar conditions may also be used if they are applicable. If the host is *E. coli*, the culture is carried out at about 30° to 37° C. for about 3 to 24 hours, if necessary under aeration or stirring. If the host is yeast, the culture is carried out at about 25° to 37° C. for about 12 hours to 2 weeks, if necessary under aeration or stirring. If the host is animal cells, the culture is carried out at about 32° to 37° C. in 5% $CO_2$ and 100% humidity for about 24 hours to 2 weeks, if necessary under stirring, and the conditions for the gaseous phase may be changed if required.

After the culture, the microorganism or cells are disrupted with a homogenizer, a French press, ultrasonication, lysozyme and/or freezing and thawing to elute FGF-5 analogous protein outside, and this protein can be obtained from the soluble fraction. If the target protein is contained in the insolubilized fraction, the microorganism or cells are disrupted and the insolubilized fraction is recovered by centrifugation, and the protein can be solubilized with e.g. a buffer containing guanidine hydrochloride. Alternatively, the microorganism or cells are disrupted directly with a buffer containing a protein denaturant such as guanidine hydrochloride etc. to elute the target protein outside.

To purify the FGF-5 analogous protein from the supernatant obtained above, a suitable combination of conventional separation and purification means can be used. Such conventional separation and purification means include salting-out, solvent precipitation, dialysis, ultrafiltration, gel filtration, SDS-polyacrylamide gel electrophoresis, ion-exchange chromatography, affinity chromatography, reverse phase high performance liquid chromatography, and isoelectric focusing. Affinity chromatography on heparin Sepharose as the carrier can further be applied to a large number of FGF-5 analogous proteins.

The preparation thus obtained may be dialyzed and lyophilized into dry powder unless the activity of the FGF-5 analogous protein is lost. The addition of serum albumin as a carrier can effectively prevent the adsorption of the preparation onto the vessel in storage.

In addition, the addition of a trace amount of a reducing agent in the purification process or in storage is effective for preventing oxidation of the preparation. The reducing agent used is β -mercaptoethanol, dithiothreitol, glutathione etc.

The FGF-5 analogous protein of the present invention regulates the mechanism of hair production, specifically for promoting or suppressing restoration of hairs on the head or promoting or suppressing hair growth.

Further, the FGF-5 analogous protein of the present invention regulates nutrition and functions in the brain nerve system.

Furthermore, the FGF-5 analogous protein of the present invention regulates the physiological functions of FGF-5 in addition to said actions. The physiological functions of FGF-5 refer specifically to promotion or suppression of proliferation or differentiation of fibroblasts, vascular endothelial cells, myoblasts, chondrocytes, osteoblasts and glia cells, or to regulation of the functions of these cells.

By virtue of said functions of the FGF-5 analogous protein, this protein is useful for prevention and treatment of various diseases, such as fibroblastoma, hemangioma, osteoblastoma, nerve cell death, Alzheimer's disease, Parkinson's disease, neuroblastoma, amnesia, dementia and myocardial infarction.

buffer, pH 8.3, 40 mM KCl, 6 mM $MgCl_2$, 1 mM DTT, 0.4 mM dNTPs and 40 units of RN asin to give a cDNA mixture.

Then, the target gene in the cDNA mixture thus obtained was amplified by PCR reaction in the following manner. The cDNA mixture, 0.5 μl, was subjected to amplification with 0.5 unit of AmpliTaq (Perkin Elmer) in the presence of 250 μM dNTPs, 75 mM $NH_4$ $O_2$ $SO_4$, pH 8.5, 2.0 mM $MgCl_2$, 0.5 μg sense primer (A, shown below) and 0.5 μg antisense primer (B, below) in 40 cycles each consisting of thermal treatment at 94° C. for 1 minute, 60° C. for 2 minutes and 72° C. for 1 minute.

A: 5'-GA ATG AGC TTG TCC TTC CTC CTC CTC CTC TTC TTC AGC CAC-3' (SEQ ID NO:5)

B: 5'-AAG TTC TGG CTG CTC CGA CTG CTT-3' (SEQ ID NO:6)

The FGF-5 analogue protein obtained as described above makes use of a pharmaceutical acceptable solvent, fillers, carriers and auxiliary agents to be formed in a usual manner into a pharmaceutical composition in the form of a liquid, lotion, aerosol, injection, powder, granules, tablets, suppositories, intestinal agent, capsules etc.

In the pharmaceutical composition, the content of the FGF-5 analogous protein as the active ingredient may range from $10^{-10}$ to 1.0% by weight.

The pharmaceutical composition can be administrated orally or parenterally and safely into mammals such as humans, mouses, rats, rabbits, dogs, cats etc. as a hair restoration agent, hair development agent, nutrition and functional suppresser in the brain and nervous system, learning effect regulator etc. The dose of the present pharmaceutical composition can be varied depending on the form of the agent, administration route, symptoms etc. For example, $10^{-4}$ to $10^3$ mg of the FGF-5 analogue protein may be administrated several times per day.

Deposition of the Microorganism

Figure 2:
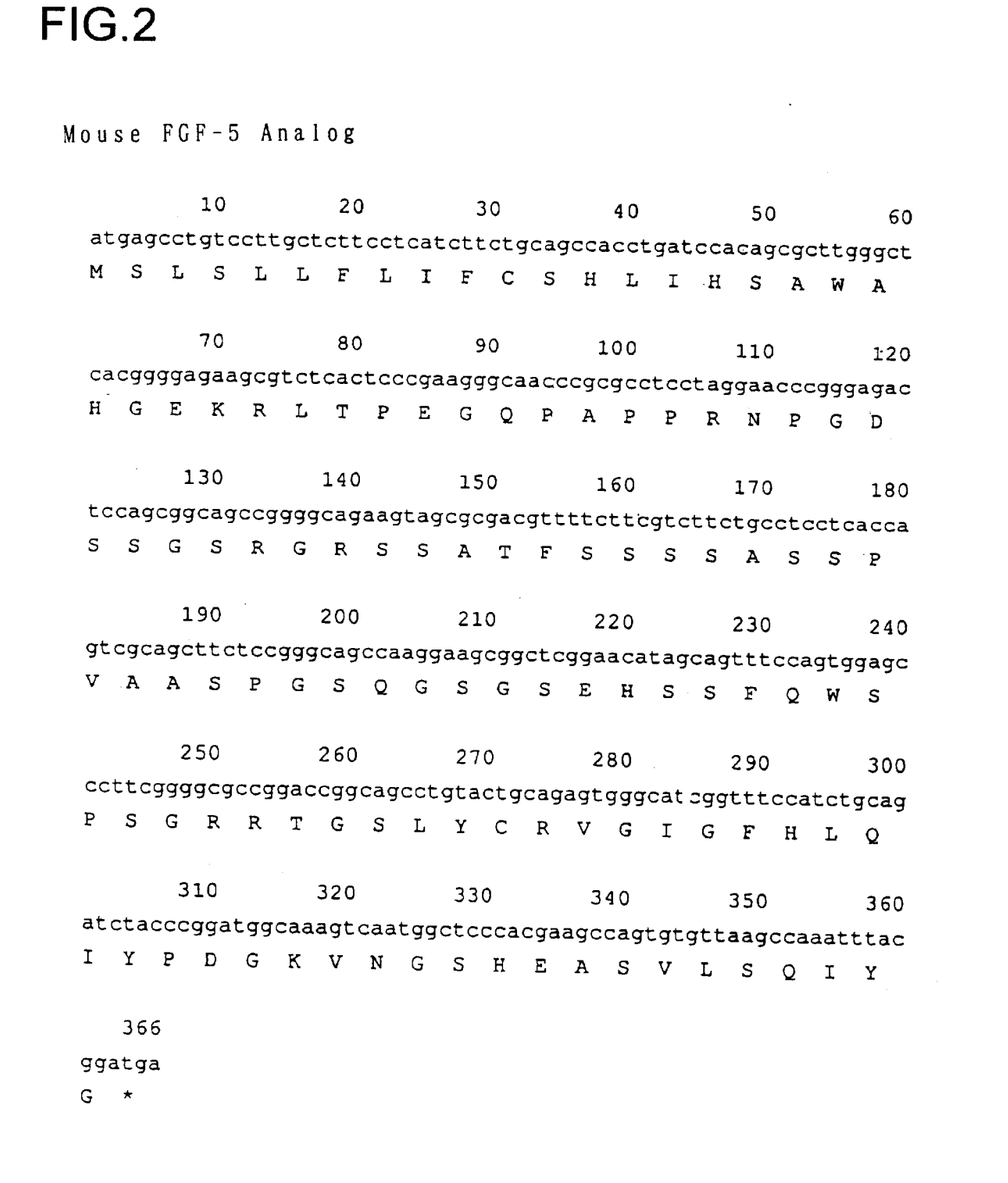
FIG. 2 shows the amino acid sequence (SEQ ID No:4) of mouse FGF-5 analogue (mouse FGF-5S) protein and a DNA sequence (SEQ ID No:3) coding for said protein.

E. coli MFGF5S/PBS/XL1 carrying a plasmid containing the gene of the DNA sequence of FIG. 2 coding for mouse FGF-5 analogous protein according to the present invention has been deposited since Mar. 12, 1996 with the National Institute of Bioscience and Human-Technology, Agency of Industrial Science and Technology, Japan.

EXAMPLES

Hereinafter, the present invention is described in detail by reference to the following examples, which however are not intended to limit the present invention.

Example 1

Preparation of cDNA coding for human FGF-5 analogue (human FGF-5S)

Human RNA, e.g. human brain whole RNA (Catalog No. 640202-1, available from Clontech) is used. To 1 μg of this human RNA was added 120 ng random hexanucleotide DNA, and reverse transcription was carried out using 200 units of M-HLV reverse transcriptase in 50 mM Tris-HCl As a result, cDNA coding for human FGF-5S was formed. The formed cDNA was cloned in pBlueScript vector and its nucleotide sequence was confirmed (FIG. 1).

Example 2

Preparation of cDNA Coding for Mouse FGF-5 Analog (Mouse FGF-5S)

The brain was isolated from a female ICR mouse, 6-week-old, and RNA was extracted from it. 120 ng random hexanucleotide DNA was added to 1 μg of the mouse RNA, and reverse transcription was carried out using 200 units of M-HLV reverse transcriptase in 50 mM Tris-HCl buffer, pH 8.3, 40 mM KCl, 6 mM $MgCl_2$, 1 mM DTT, 0.4 mM dNTPs and 40 units of RN asin to give a cDNA mixture.

Then, the target gene in the cDNA mixture thus obtained was amplified by PCR reaction in the following manner. The cDNA mixture, 0.5 μl, was subjected to amplification with 0.5 unit of AmpliTaq (Perkin Elmer) in the presence of 250 μM dNTPs, 75 mM $NH_4$ $O_2$ $SO_4$, pH 8.5, 2.0 mM $MgCl_2$, 0.5 μg sense primer (C, shown below) and 0.5 μg antisense primer (D, below) in 40 cycles each consisting of thermal treatment at 94° C. for 1 minute, 60° C. for 2 minutes and 72° C. for 1 minute.

C: 5'-AAGAATGAGCCTGTCCTTGCTCTTCCTCATCTTCTGCAGCCACCTGATCCA-3' (SEQ ID NO:7)

D: 5'-AAGTTCCGGTTGCTCGGACTGCTT-3' (SEQ ID NO:8)

As a result, cDNA coding for the target mouse FGF-5S was formed. The formed cDNA was cloned in pBlueScript vector, and its nucleotide sequence was confirmed (FIG.2).

Example 3

Expression a nd Identi fication of Mouse FGF-5 Analog

Figure 3:
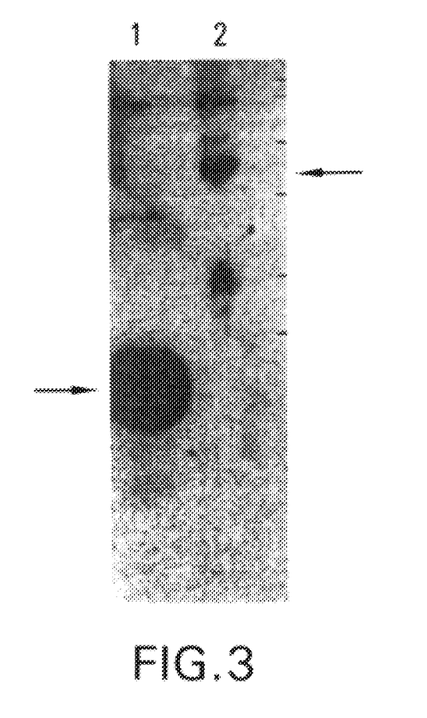
FIG. 3 shows a photograph of mouse FGF-5S protein and human FGF protein in SDS-polyacrylamide gel electrophoresis.

As a template, the vector carrying the cDNA coding for mouse FGF-5S i nserted into a region downstream of T7 promoter was transcribed and translated in a usual manner, and the translational product was separated by SDS-polyacrylamide gel electrophoresis and transferred onto a nitrocellulose membrane. This membrane was incubated with an anti-FGF-5 rabbit antibody and the antibody-bound molecule was detected with a HRP-labeled anti-rabbit antibody in a chemiluminescence method. The results are shown in FIG. 3. Lane 1 is the prepared FGF-5S protein, and lane 2 is whole-length FGF-5 produced by E. coli. It was confirmed that the FGF-5S cDNA codes for the protein molecule with a molecular weight of about 14,000 and the protein has an epitope in common with FGF-5, and simultaneously the protein was obtained.

Example 4

Confirmation of Expression of FGF-5 Analog (FGF-5S) mRNA by RNase Protection Assay Mouse FGF-5 cDNA inserted into pBluescript vector (Stratagene) was transcribed in the presence of labeled RNA precursors to synthesize a 652-bp labeled riboprobe capable of hybridizing to a part of FGF-5 mRNA corresponding to the whole region of exons 1, 2 and 3 in FGF-5 gene. Whole RNA was extracted from mouse cells derived from the nerve cells, then mixed with and hybridized to the above labeled riboprobe under suitable conditions, and the RNA not hybridized to the probe was removed by digestion with RNase T1. The hybridized RNA was electrophoresed to determine molecular weight. As a result, 326-bp and 222-bp reaction products showing the presence of the FGF-5 analog (FGF-5S) mRNA were detected along with a 652-bp reaction product showing the presence of the FGF-5 mRNA. This indicated the presence of the FGF-5 analog (FGF-5S) mRNA in nerve cells.

Example 5

Expression of FGF-5 Analog (FGF-5S) Protein in E. coli and Its Purification Human FGF-5 analog (FGF-5S) cDNA was inserted into a region downstream from a sequence coding for maltose-binding protein (MBP) contained in fusion protein expression plasmid vector pMAL-c2 (New England Biolabs) to construct expression plasmid pMAL/humFGF5S. E. coli was transformed with this plasmid and cultured in a liquid medium. The expression of a MBP-FGF5S fusion protein was induced by adding isopropylgalactopyranoside in the latter period of culture. The microorganism was disrupted by ultrasonication to release the fusion protein, and this fusion protein was purified through an affinity column on amylose resin (New England Biolabs). The fusion protein thus obtained was cleaved with a specific proteolytic enzyme Factor Xa (New England Biolabs) to give MBP and FGF-5 analog (FGF-5S) protein, and the FGF-5 analog protein was then separated. As a result, high-purity FGF-5 analog (FGF-5S) protein could be obtained in a large amount.

Example 6

Regulatory Action of FGF-5 Analog (FGF-5S) Protein on Cell Proliferation Induced by FGF-5 Protein The FGF-5 protein was added to a culture liquid of cultured fibroblast mouse 3T3 cells under serum starvation, and cell proliferation was evaluated by determining the amount of DNA synthesized by the cells from 15 to 19 hours after the initiation of culture. As a result, the amount of synthesized DNA was increased depending on the amount of the FGF-5 protein added to the culture, indicating that the FGF-5 protein possessed cell proliferation activity. On the other hand, the synthesis of DNA by cells was inhibited when the cells were cultured in the presence of both the FGF-5 protein and FGF-5 analog (FGF-5S) protein. This is an example where the FGF-5 analog (FGF-5S) protein regulates the proliferation of cells by the FGF-5 protein.

Example 7

Regulatory Action of FGF-5 Analog (FGF-5S) Protein on Neurotrophic Activity of FGF-5

Human FGF-5 analog (FGF-5S) cDNA and human FGF-5 cDNA were inserted into cloning sites in animal cell expression vector pMEXneo to construct expression plasmids pMEX/FGF-5S and pMEX/FGF-5, respectively. PC12 cells, i.e. model cells for nerve differentiation, were transformed with either or both of plasmids pMEX/FGF-5S and pMEX/FGF-5 and examined for their acetylcholine esterase activity. This acetylcholine esterase activity serves as an indicator for the nerve differentiation of PC12 cells and can thus be used to evaluate neurotrophic activity. In this experiment, the PC12 cells having the FGF-5 solely showed nerve differentiation, while the PC12 cells having both the FGF-5 and FGF-5 analog (FGF-5S) hardly showed nerve differentiation. This is an example where the FGF-5 analog (FGF-5S) regulates trophic activity of FGF-5 on nervous system.

Effect of the Invention

According to the pharmaceutical composition with the novel FGF-5 analogous protein of the present invention as an active ingredient, it is possible to regulate the physiological functions of FGF-5, such as regulation of restoration or development of hairs on the head or body, trophic or functional regulation in the brain nerve system, proliferation of fibroblasts, etc.

What is claimed is:

1. An isolated and purified FGF-5 protein having the amino acid sequence as set forth in SEQ ID NO: 2.

2. An isolated and purified FGF-5 protein having the amino acid sequence as set forth in SEQ ID NO: 4.

3. An isolated and purified DNA molecule having a nucleotide sequence coding for the amino acid sequence as set forth in SEQ ID NO: 2.

4. An isolated and purified DNA molecule having a nucleotide sequence coding for the amino acid sequence as set forth in SEQ ID NO: 4.

5. An isolated and purified DNA molecule having the nucleotide sequence as set forth in SEQ ID NO: 1.

6. An isolated and purified DNA molecule having the nucleotide sequence as set forth in SEQ ID NO: 3.

7. A pharmaceutical composition comprising the protein of claim 1 and a pharmaceutically acceptable carrier.

8. A pharmaceutical composition comprising the protein of claim 2 and a pharmaceutically acceptable carrier.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear     ( i x ) FEATURE:
        ( A ) NAME/KEY: None
        ( B ) LOCATION: 1...369

(D) OTHER INFORMATION:

(xi) SEQUENCE DESCRIPTION: SEQ ID NO:1:

| | | | | | |
|---|---|---|---|---|---|
| ATGAGCTTGT | CCTTCCTCCT | CCTCCTCTTC | TTCAGCCACC | TGATCCTCAG | CGCCTGGGCT | 60 |
| CACGGGGAGA | AGCGTCTCGC | CCCCAAAGGG | CAACCCGGAC | CCGCTGCCAC | TGATAGGAAC | 120 |
| CCTATAGGCT | CCAGCAGCAG | ACAGAGCAGC | AGTAGCGCTA | TGTCTTCCTC | TTCTGCCTCC | 180 |
| TCCTCCCCCG | CAGCTTCTCT | GGGCAGCCAA | GGAAGTGGCT | TGGAGCAGAG | CAGTTTCCAG | 240 |
| TGGAGCCCCT | CGGGGCGCCG | GACCGGCAGC | CTCTACTGCA | GAGTGGGCAT | CGGTTTCCAT | 300 |
| CTGCAGATCT | ACCCGGATGG | CAAAGTCAAT | GGATCCCACG | AAGCCAATAT | GTTAAGCCAA | 360 |
| GTTCACAGAT | GA | | | | | 372 |

(2) INFORMATION FOR SEQ ID NO:2:

(i) SEQUENCE CHARACTERISTICS:
(A) LENGTH: 123 amino acids
(B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:2:

```
Met  Ser  Leu  Ser  Phe  Leu  Leu  Leu  Leu  Phe  Phe  Ser  His  Leu  Ile  Leu
 1              5                        10                       15

Ser  Ala  Trp  Ala  His  Gly  Glu  Lys  Arg  Leu  Ala  Pro  Lys  Gly  Gln  Pro
              20                        25                       30

Gly  Pro  Ala  Ala  Thr  Asp  Arg  Asn  Pro  Ile  Gly  Ser  Ser  Ser  Arg  Gln
              35                        40                       45

Ser  Ser  Ser  Ser  Ala  Met  Ser  Ser  Ser  Ala  Ser  Ser  Ser  Pro  Ala
      50                        55                       60

Ala  Ser  Leu  Gly  Ser  Gln  Gly  Ser  Gly  Leu  Glu  Gln  Ser  Ser  Phe  Gln
 65                       70                        75                       80

Trp  Ser  Pro  Ser  Gly  Arg  Arg  Thr  Gly  Ser  Leu  Tyr  Cys  Arg  Val  Gly
                    85                        90                       95

Ile  Gly  Phe  His  Leu  Gln  Ile  Tyr  Pro  Asp  Gly  Lys  Val  Asn  Gly  Ser
                   100                       105                      110

His  Glu  Ala  Asn  Met  Leu  Ser  Gln  Val  His  Arg
              115                       120
```

(2) INFORMATION FOR SEQ ID NO:3:

(i) SEQUENCE CHARACTERISTICS:
(A) LENGTH: 366 base pairs
(B) TYPE: nucleic acid
(C) STRANDEDNESS: single
(D) TOPOLOGY: linear (ix) FEATURE:
(A) NAME/KEY: None
(B) LOCATION: 1...363
(D) OTHER INFORMATION:

(xi) SEQUENCE DESCRIPTION: SEQ ID NO:3:

| | | | | | |
|---|---|---|---|---|---|
| ATGAGCCTGT | CCTTGCTCTT | CCTCATCTTC | TGCAGCCACC | TGATCCACAG | CGCTTGGGCT | 60 |
| CACGGGGAGA | AGCGTCTCAC | TCCCGAAGGG | CAACCCGCGC | CTCCTAGGAA | CCCGGGAGAC | 120 |
| TCCAGCGGCA | GCCGGGGCAG | AAGTAGCGCG | ACGTTTTCTT | CGTCTTCTGC | CTCCTCACCA | 180 |
| GTCGCAGCTT | CTCCGGGCAG | CCAAGGAAGC | GGCTCGGAAC | ATAGCAGTTT | CCAGTGGAGC | 240 |

-continued

```
CCTTCGGGGC    GCCGGACCGG    CAGCCTGTAC    TGCAGAGTGG    GCATCGGTTT    CCATCTGCAG         300

ATCTACCCGG    ATGGCAAAGT    CAATGGCTCC    CACGAAGCCA    GTGTGTTAAG    CCAAATTTAC         360

GGATGA                                                                                  366
```

( 2 ) INFORMATION FOR SEQ ID NO:4:

( i ) SEQUENCE CHARACTERISTICS:
    ( A ) LENGTH: 121 amino acids
    ( B ) TYPE: amino acid
    ( C ) STRANDEDNESS: single
    ( D ) TOPOLOGY: linear   ( i i ) MOLECULE TYPE: protein   ( v ) FRAGMENT TYPE: internal   ( x i ) SEQUENCE DESCRIPTION: SEQ ID NO:4:

```
Met  Ser  Leu  Ser  Leu  Leu  Phe  Leu  Ile  Phe  Cys  Ser  His  Leu  Ile  His
  1              5                        10                         15

Ser  Ala  Trp  Ala  His  Gly  Glu  Lys  Arg  Leu  Thr  Pro  Glu  Gly  Gln  Pro
               20                        25                        30

Ala  Pro  Pro  Arg  Asn  Pro  Gly  Asp  Ser  Ser  Gly  Ser  Arg  Gly  Arg  Ser
          35                        40                        45

Ser  Ala  Thr  Phe  Ser  Ser  Ser  Ala  Ser  Ser  Pro  Val  Ala  Ala  Ser
     50                        55                        60

Pro  Gly  Ser  Gln  Gly  Ser  Gly  Ser  Glu  His  Ser  Ser  Phe  Gln  Trp  Ser
 65                         70                        75                        80

Pro  Ser  Gly  Arg  Arg  Thr  Gly  Ser  Leu  Tyr  Cys  Arg  Val  Gly  Ile  Gly
                    85                        90                         95

Phe  His  Leu  Gln  Ile  Tyr  Pro  Asp  Gly  Lys  Val  Asn  Gly  Ser  His  Glu
              100                       105                       110

Ala  Ser  Val  Leu  Ser  Gln  Ile  Tyr  Gly
              115                      120
```

( 2 ) INFORMATION FOR SEQ ID NO:5:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:5:

```
GAATGAGCTT    GTCCTTCCTC    CTCCTCCTCT    TCTTCAGCCA    C                              41
```

( 2 ) INFORMATION FOR SEQ ID NO:6:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear   ( x i ) SEQUENCE DESCRIPTION: SEQ ID NO:6:

```
AAGTTCTGGC    TGCTCCGACT    GCTT                                                       24
```

( 2 ) INFORMATION FOR SEQ ID NO:7:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

AAGAATGAGC CTGTCCTTGC TCTTCCTCAT CTTCTGCAGC CACCTGATCC A    51

( 2 ) INFORMATION FOR SEQ ID NO:8:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear   ( x i ) SEQUENCE DESCRIPTION: SEQ ID NO:8:

AAGTTCCGGT TGCTCGGACT GCTT    24